United States Patent
Raj et al.

(10) Patent No.: US 6,893,849 B2
(45) Date of Patent: May 17, 2005

(54) **FERMENTATION PROCESS FOR PRODUCTION OF XYLITOL FROM *PICHIA SP***

(75) Inventors: Arulmuthu Eugene Raj, Karnataka (IN); Marichetti Kuppuswami Gowthaman, Karnataka (IN); Nandan Prakash Ghildyal, Karnataka (IN); Mahesh Chandra Mishra, Karnataka (IN); Ganesh Karanth Naikankatte, Karnataka (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 10/703,088

(22) Filed: Nov. 7, 2003

(65) Prior Publication Data

US 2004/0191881 A1 Sep. 30, 2004

Related U.S. Application Data

(60) Provisional application No. 60/458,403, filed on Mar. 31, 2003.

(51) Int. Cl.$^7$ ............................. C12P 7/18; C12N 1/16
(52) U.S. Cl. ................ 435/158; 435/254.23; 435/254.2
(58) Field of Search ................................. 435/158, 157, 435/155, 132, 41, 254.2, 254.23, 243

(56) References Cited

PUBLICATIONS

Parajo, J.C., et al. 1998. Biotechnological production of xylitol, part 2: Operation in culture media made with commercial sugars. Bioresource Technology 65: 203–212.*

Furlan, S.A., et al. 1994. Influence of oxygen on ethanol and xylitol production by xylose fermenting yeasts. Process Biochemistry 29: 657–662.*

Suryadi, H., et al. 2000. Polyol production by culture of methanol–utilizing yeast. J. Bioscience and Bioengineering 89: 236–240.*

Delgenes, J.P., et al. 1998. Biological production of industrial chemicals, i.e. xylitol and ethanol, from lignocelluloses by controlled mixed culture systems. Industrial Crops and Products 7: 101–111.*

Rodrigues, D.C.G.A., et al. 1999. Fed–batch culture of *Candida guilliermondii* FTI 20037 for xylitol production from sugar cane bagasse hydrolysate. Letters in Applied Microbiology 29: 359–363.*

* cited by examiner

*Primary Examiner*—Sandra Saucier
*Assistant Examiner*—Lora E Barnhart
(74) *Attorney, Agent, or Firm*—Foley & Lardner LLP

(57) ABSTRACT

The present invention deals with an improved fermentation process for the production of xylitol from *Pichia* sp. and the said process is submerged fermentation for the production of xylitol using cotton seed flour as cheap organic nitrogen source and the main advantage is short fermentation time and higher yield of xylitol from xylose moreover, one of the essential aspects of the present invention is that the medium for the fermentation using *Pichia* sp. for producing high yield of xylitol from xylose has been obtained using a specific combination of nutritional parameters.

19 Claims, No Drawings

FERMENTATION PROCESS FOR PRODUCTION OF XYLITOL FROM PICHIA SP

This application claims benefit of Provisional 60/458,403 filed Mar. 31, 2003

FIELD OF THE INVENTION

The present invention relates to an improved fermentation process for the production of xylitol using *Pichia* sp. The various nutritional parameters of fermentation medium have also been optimized in this invention, which is responsible for the higher xylitol production.

BACKGROUND AND PRIOR ART

Xylitol is a low-calorie sweetener, which is increasingly used in food, pharmaceutical and oral health products. It is a naturally occurring five-carbon sugar alcohol (polyol). Emil Fischer, a German chemist, discovered it in 1891. It is used as a sweetening agent in human food since the 1960s and is a white crystalline powder, odorless and has a pleasant taste. Xylitol is found in many fruits and vegetables and also produced by human body during normal metabolism. It is the sweetest of all polyols. It is as sweet as sucrose and has no after taste and is suitable for diabetics. It has 40% less calories than sucrose (EU, US) and has a calorific value of 2.4 kcal/gm. It is the only sweetener with conclusive data on caries prevention and has strong cariostatic potential. It has also gained importance in the prevention of acute otitis media (most common ear infection in children).

Xylitol can be produced by either chemical or biological methods, usually being produced by the chemical reduction of xylose derived from hemicellulosic fractions of birchwood or other xylose-rich materials. Xylitol is produced commercially by extraction from birch wood or other hemicellulosic material such as bagasse, which is rich in xylans. The fermentation of xylan rich material to xylose has been reported in literature. Yeasts generally produce Xylitol. The biosynthetic pathway involves isomerisation of D-Xylose to D-xylulose by xylose isomerase and reduction to xylitol by NADH-dependent xylitol dehydrogenase or reduction by xylose reductase in the presence of NADPH or NADH.

Reference may be made Yong. K. S. et al in "Fermentation process for preparing xylitol using *Candida tropical* is in U.S. Pat. No. 5,998,181, 1999 wherein the authors have reported a xylitol yield of 19.6% based on D-xylulose from *Pichia farinosa* ATCC 20216) and a yield of 48% from *Zygosaccharomyces polymorphus*.

Reference may be made to Yong. K. S. et al. in Fermentation process for preparing xylitol using mutant cells" in U.S. Pat. No. 5,686,277, 1997 wherein the authors have reported a xylitol yield of 80–85% based on xylose from *Candida parapsilosis* (KCCM 10088).

Reference may be made to Heikki. O. et al in 'Process for the preparation of xylitol from xylose by cultivating *Candida guilliermondif* in WO patent No. 8805467, 1988 wherein the authors have reported a xylitol yield of 63–78% based on xylose from *Candida guilliermondii* (VTT-C-71QQ6) by fed-batch fermentation.

Reference may be made to Rahkila, L. et al., in "Method for the production of xylitol" in U.S. Pat. No. 5,081,026, 1992 wherein the authors have reported a xylitol yield of 50% based on xylose from *Debaryomyces hansenii*.

Reference may be made to Walther, T et al. [*Bioresource-Technol.* 76:3, 213–220. 2001] wherein the authors have reported a maximum xylitol yield of 84% from *Andida tropicalis* based on xylose.

Reference may be made to Choi, H. et al [*Biotechnol. Lett.* 22:20. 1625–1628, 2000] wherein the authors have reported a maximum xylitol yield of 82% from *Candida tropicalis* (ATCC 3803) based on xylose.

Reference may be made to Bao. X. et al [*Ind. Microbiol.* 30:2, 3–18, 2000] wherein the authors have reported a maximum xylitol Yield of 94% from a recombinant strain of *Saccharomyces cerevisiae* (strain HYEX2) using recombinant xylose reductase gene.

Reference may be made to Tavares. J. M. et al. [*Enzyme Microb. Technol.* 26:9–10. 743–747. 2000] wherein the authors have reported a maximum xylitol yield of 56% based on xylose from *Debaryomyces hansenii* (CCMI 941).

Reference may be made to Nakano, K. et al. [*J.Ferment.Bioeng.* 89:4, 372–376, 2000], wherein the authors have reported a maximum xylitol yield of 82% based on xylose from *Candida magnoliae* TISTR5663.

Reference may be made to Suryadi. H et al., [*J.Ferment.Bioeng.* 89:3, 236–240, 2000] wherein the authors have reported a maximum xylitol yield of 46% based on xylose from *Hansenula polymorpha* DL1 (AKU 4327).

Reference may be made to Converti, A. et al., [*Appl.Biochem.Biotechnol.* 82:2, 141–151. 2000] wherein the authors have reported a maximum xylitol yield of 63% based on xylose from *Pachysolen tannophilus* (NRRL Y-2460).

Reference may be made to Preziosi, B. L. et al., [*Biotechnol.Lett.* 22:3, 239–243, 2000] wherein the authors have reported a maximum xylitol yield of 80% based on xylose from *Candida guilliermondii* (NRC 5578).

Reference may be made to Rodrigues, D. C. G. A et al., [*Lett.Appl.Microbiol.* 29:6, 359–363. 1999] wherein the authors have reported a maximum xylitol yield of 84% based on xylose from *Candida guilliermondii* (FTI 20037).

Reference may be made to U.S. Patent. No. US 2002164731 entitled, "Process for the simultaneous production of xylitol and ethanol" indicates a fermentation time of 24 to 96 hrs, however, the yields of xylitol was poor.

Reference may be made to Parajo, et.al. [*Bioresource Technol.* 65, 203–212, 1998] wherein the review paper shows the fermentation time ranges from 24–800 hours, depending on the culture used for xylitol production. The cultures producing xylitol in a fermentation time shorter than 72 hours have low xylitol yields based on xylose, with the only exception of a mixed culture of *C. pelliculosa* and *Methanobacterium* sp. where the yields were 1 g of xylitol $g^{-1}$ of xylose. The draw back of the above said process was maintenance of consortium of bacterial strains and higher operating cost.

The drawback of the above references cried by various authors is relatively low yields of xylitol. Since, the final concentration of xylitol depends on the amount of xylose used, the xylitol yield from xylose represents the efficiency of the culture to produce xylitol. A summary of the fermentative yield of xylitol from xylose for different strains is shown in Table 1.

OBJECT OF THE INVENTION

The main object of the present invention is to provide an improved fermentation process for the production of xylitol from *Pichia* sp, which obviates the drawback as detailed above.

Another object of the present invention is to obtain a high yield of xylitol from xylose.

Another object of the present invention is the use of cottonseed flour as an organic nitrogen source and inducer for xylitol production.

Yet another object of the present invention is to obtain a high productivity of xylitol from xylose using *Pichia* sp., which obviates the drawbacks as detailed above.

SUMMARY

The present invention deals with an improved fermentation process for the production of xylitol from *Pichia* sp. and the said process is submerged fermentation for the production of xylitol using cotton seed flour as cheap organic nitrogen source and the main advantage is short fermentation time and higher yield of xylitol from xylose.

The novelty of the present invention is that a medium for the fermentation of *Pichia* sp. producing high yield of xylitol from xylose has been developed using a specific combination of nutritional parameters.

DETAILED DESCRIPTION OF THE PRESENT INVENTION

The present invention deals with an improved fermentation process for the production of xylitol from *Pichia* sp. and the said process is submerged fermentation for the production of xylitol using cotton seed flour as cheap organic nitrogen source. The main advantage is short fermentation time and higher yield of xylitol from xylose. One of the essential aspects of the present invention is that the medium for the fermentation using *Pichia* sp. for producing high yield of xylitol from xylose has been obtained using a specific combination of nutritional parameters. The applicant surprisingly noticed that the quality of the protein and other vital growth factors present in the cotton seed flour are responsible for high yield of xylitol from xylose. The production levels of xylitol thus obtained are significantly higher than the values reported earlier.

In addition to serving as an organic nitrogen source, cottonseed flour contains vital growth factors such as amino acids, vitamins, fats/fatty acids, minerals, sterols and carbohydrates are available in the same source, which can greatly influence biomass formation for high xylitol yields. The use of glycerol in the production medium as a carbon source results in maximum utilization of substrate to biomass, which influences high xylitol yields.

Accordingly the present invention provides a submerged fermentation process for the production of xylitol from *Pichia* sp., which comprises a. developing inoculum for the fermentation by taking a loopful of culture from a 24 h old YMPD agar slant comprising the following nutrients (% w/v)
  (i) yeast extract 0.3–0.5.
  (ii) malt extract 0.3–0.5,
  (iii) peptone 0.5–1.0
  (iv) dextrose 1–5.
  (v) agar 2–2.5
and inoculating in 10 ml sterile media containing the following ingredients (in % w/v)
  i. glycerol 2.0–5.0,
  ii. xylose 4.0–6.0,
  iii. yeast extract 0.1–1.0,
  iv. peptone 0.5–0.2,
  v. ammonium chloride 0.1–1.0,
  vi. dipotassium hydrogen phosphate 0.1–0.5,
  vii. potassium dihydrogen orthophosphate 0.1–0.5,
  viii. ferrous sulphate 0.001–0.01,
  ix. magnesium sulphate 0.01–0.1 at a final pH of 6.0;

b) growing the culture for 18–24 hours at 30±1° C. in a shaker at 200–300 rpm (this constitutes the inoculum);

c) transferring the inoculum to a 500 mL Erlenmeyer flask containing 100 mL of sterile production media containing the following ingredients (in % w/v)
  (i) glycerol 2.0–5.0,
  (ii) xylose 2.0–5.0,
  (iii) cotton seed flour 1.0–5.0,
  (iv) ammonium chloride 0.1–1.0,
  (v) dipotassium hydrogen phosphate 0.1–0.5,
  (vi) potassium dihydrogen orthophosphate 0.1–0.5,
  (vii) ferrous sulphate 0.001–0.01,
  (viii) magnesium sulphate 0.01–0.1;

d) fermenting conditions optimum for production are 200–300 rpm at 30±1° C.;

e) carrying out fermentation for 2–3 days with a yield of 0.93–0.99 g xylitol/g xylose.

In an embodiment of the present invention, wherein the preferred concentration of the ingredients (in % w/v) in the medium are as follows: glycerol—2.5, xylose—5.0, cotton seed flour—4, ammonium chloride—0.4, dipotassium hydrogen phosphate—0.1, potassium dihydrogen orthophosphate—0.1, ferrous sulphate—0.005, magnesium sulphate—0.05.

In another embodiment of the present invention, the yeast culture used for production of xylitol by submerged fermentation is *Pichia farinosa* ATCC 20210, DSM 3316 and NRRL Y-7553.

In yet another embodiment of the present invention, fermentation time of 48–72 hrs is required for maximum conversion of xylose to xylitol.

In still another embodiment of the present invention, high yields of 0.93 to 0.99 g xylitol g xylose are obtained.

A schematic of the fermentation process for the production of xylitol from *Pichia* sp. is described below.

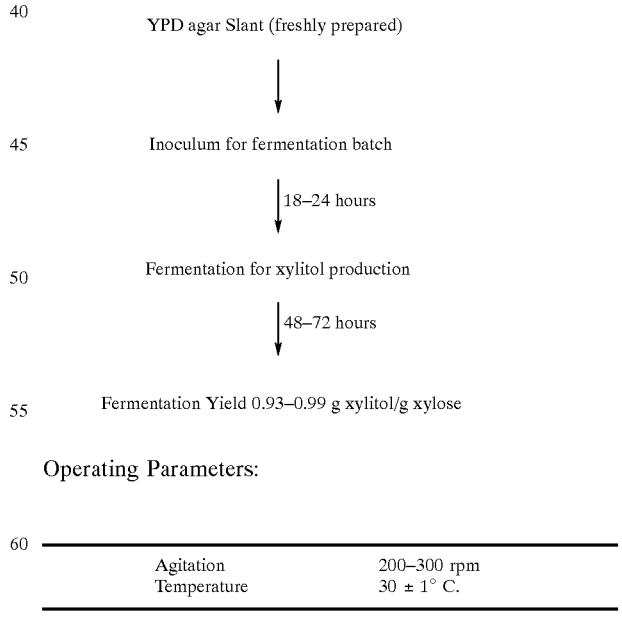

Operating Parameters:

| Agitation | 200–300 rpm |
| Temperature | 30 ± 1° C. |

The preferred microorganisms from the *Phichia* sp. used in this invention are *Pichia farinosa* ATCC 20210, DSM 3316 and NRRL Y-7553. The xylitol and xylose concentration in the broth was determined after centrifugation of 10-mL fermenter broth at 10,000 g for 10 minutes at 4° C. and estimating by Shimadzu HPLC using a Supelcogel carbohydrate column (C-610H) with 0.5 mL/min of 0.1% $H_3PO_4$ as the mobile phase at a retention time of 14.4 and 12.8 min respectively.

Brief Description of Table

Table 1 Fermentative Yield of Xylitol from Xylose for Different Strains

EXAMPLES

The following examples are given by way of illustration of the present invention only and therefore should not be construed to limit the scope of the invention.

Example—1

In a 100 mL Erlenmeyer flask containing 10 mL of medium containing the following ingredients (in % w/v) glycerol—2.5, xylose—5.0, yeast extract—0.5, peptone—1.0, ammonium chloride—0.4, dipotassium hydrogen phosphate—0.1, potassium dihydrogen orthophosphate—0.1, ferrous sulphate—0.005, magnesium sulphate—0.05 at a final pH of 6.0; the culture is grown for 18–24 hours at 30±1° C. in a shaker at 200–300 rpm (this constitutes the inoculum); fermentation experiments were carried out in 500 mL Erlenmeyer flask containing 100 mL of sterile production media containing the following ingredients (in % w/v) glycerol—2.5, xylose—5.0, cotton seed flour—3, ammonium chloride—0.4. dipotassium hydrogen phosphate—0.1, potassium dihydrogen orthophosphate—0.1. ferrous sulphate—0.005, magnesium sulphate—0.05 by using the, inoculum and incubating in a shaker of 200–300 fpm at 30±1° C.; the fermentation is carried out for 3 days and a xylitol concentration of 47 g/L was obtained; the fermentation yield obtained was 0.94 g xylitol/ g xylose.

Example—2

In a 100 mL Erlenmeyer flask containing 10 mL of medium containing the following ingredients (in % w/v) glycerol—2.5, xylose—5.0, yeast extract—0.5, peptone 1.0. ammonium chloride—0.4, dipotassium hydrogen phosphate—0.1, potassium dihydrogen orthophosphate—0.1, ferrous sulphate—0.005, magnesium sulphate—0.05 at a final pH of 6.0; the culture is grown for 18–24 hours at 30±PC in a shaker at 200–300 rpm (this constitutes the inoculum); fermentation experiments were carried out in 500 mL Erlenmeyer flask containing 100 mL of sterile production media containing the following ingredients (in % w/v) glycerol—2.5, xylose—5.0, cotton seed flour—4, ammonium chloride—0.4, dipotassium hydrogen phosphate—0.1, potassium dihydrogen orthophosphate—0.1, ferrous sulphate—0.005, magnesium sulphate—0.05 by using the inoculum and incubating in a shaker of 200–300 rpm at 30±1° C.; the fermentation is carried out for 3 days and a xylitol concentration of 49.5 g/L was obtained; the fermentation yield obtained was 0.99 g xylitol/g xylose.

Example—3

In a 100 mL Erlenmeyer flask containing 10 mL of medium containing the following ingredients (in % w/v) glycerol—2.5, xylose—5.0, yeast extract—0.5, peptone 1.0. ammonium chloride—0.4, dipotassium hydrogen phosphate—0.1, potassium dihydrogen orthophosphate—0.1, at a final pH of 6.0; the culture is grown for 18–24 hours at 30±1°° C. in a shaker at 200–300 rpm (this constitutes the inoculum); fermentation experiments were carried out in 500 mL Erlenmeyer flask containing 100 mL of sterile production media containing the following ingredients (in % w/v) glycerol—2.5, xylose—5.0. cottonseed flour—2, ammonium chloride—0.4, dipotassium hydrogen phosphate—0.1, potassium dihydrogen orthophosphate—0.1, ferrous sulphate—0.005, magnesium sulphate—0.05 by using the inoculum and incubating in a shaker of 200–300 rpm at 30±1° C.; the fermentation is carried out for 3 days and a xylitol concentration of 46.6 g/L was obtained; the fermentation yield obtained was 0.97 g xylitol/g xylose.

Though, the problems encountered in the various prior art have been given, yet the applicants substantiate the advantages of the present invention over the prior art by providing a summary of the fermentative yield of xylitol from xylose for different strains is shown in Table 1.

TABLE 1

| No | Strain | Xylitol yield (%) g xylitol/ g xylose | Ref.* |
|---|---|---|---|
| 1. | *Pichia farinosa* (ATCC 20216) | 19.6 | 1 |
|  | *Zygosaccharomyces polymorphus* | 48 |  |
| 2. | *Candida parapsilosis* (KCCM 10088) | 80–85 | 2 |
| 3. | *Candida guilt iermondii* (VTT-C-71006) | 63–78 | 3 |
| 4. | *Debaryomyces hansenii* | 50 | 4 |
| 5 | *Candida tropicalis* | 84 | 5 |
| 6 | *Candida tropicalis* (ATCC 13803) | 82 | 6 |
| 7 | *Saccharomyces cerevisiae* (strain HYEX2)[+] | 94 | 7 |
| 8 | *Debaiyomyces hansenii* (CCM1 941) | 56 | 8 |
| 9 | *Candida magnolias* TISTR5663 | 82 | 9 |
| 10 | *Hansenula polymorpha* DL1 (AKU 4327) | 46 | 10 |
| 11 | *Pachysolen lannophilus* (NRRL Y-2460) | 63 | 11 |
| 12 | *Candida guiliiermondii* (NRC 5578) | 80 | 12 |
| 13 | *Candida gmlliermondii* (FTI 20037) | 84 | 13 |
| 14 | *Pichia* sp. | 93–99 | This invention |

*References cited in the text are in the same order
[+]Recombinant strain

The main advantages of the present invention are:
1. The production of high yields of xylitol from *Pichia* sp.
2. Use of a cheap organic nitrogen source like cottonseed flour for production of xylitol.
3. A short fermentation time of 48–72 hrs for the maximum conversion of xylitol to xylose.

We claim:

1. A submerged fermentation process for the production of xylitol using yeast strains which comprises the following steps:
   a) obtaining an inoculum of yeast strain *Pichia* sp.;
   b) inoculating the inoculum in a 10 ml sterile medium containing the ingredients (% w/v) glycerol within a range of 2.0–5.0, xylose within a range of 4.0–6.0, yeast extract within a range of 0.1–1.0, peptone within a range of 0.5–2.0, ammonium chloride within a range of 0.1–1.0, dipotassium hydrogen phosphate within a range of 0.1–0.5, potassium dihydrogen orthophosphate within a range of 0.1–0.5, ferrous sulphate within a range of 0.001–0.01 and magnesium sulphate within a range of 0.01–0.1 at a final pH in the range of 5.5 to 6.5;
   c) growing the inoculum for 18–24 hours at 30±1° C. in a shaker at 200–300 rpm, and
   d) fermenting the sterile medium containing the following ingredients (in % w/v) glycerol within a range of 2.0–5.0, xylose within a range of 2.0–5.0, cotton seed flour within a range of 1.0–5.0, ammonium chloride within a range of 0.1–1.0, dipotassium hydrogen phosphate within a range of 0.1–0.5, potassium dihydrogen orthophosphate within a range of 0.1–0.5, ferrous sulphate within a range of 0.001–0.01 and magnesium sulphate within a range of 0.01–0.1 using the inoculum of step (c) under stirring at 30±1° C. for 24–90 hours and obtaining the xylitol.

2. The process as claimed in claim 1, wherein said yeast strain species is *Pichia farinosa*.

3. The process as claimed in claim 1, wherein the said yeast strain is *Pichia farinosa* having the accession number ATCC 20210, DSM 3316, or NRRL Y-7553.

4. The process as claimed in claim 1, wherein the medium containing the ingredients of step 1(b) and (d) is water.

5. The process as claimed in claim 1, wherein in the pH of the medium of step (b) is about 6.0.

6. The process as claimed in claim 1, wherein in the step (d) the concentration of glycerol for fermentation media is 2.5 (in % w/v).

7. The process as claimed in claim 1, wherein in the step (d) the concentration of xylose for fermentation media is 5.0 (in % w/v).

8. The process as claimed in claim 1, wherein in the step (d) the concentration of yeast extract for fermentation media is 0.5 (in % w/v).

9. The process as claimed in claim 1, wherein in the step (d) the concentration of peptone for fermentation media is 1.0 (in % w/v).

10. The process as claimed in claim 1, wherein in the step (d) the concentration of ammonium chloride for fermentation media is 0.4 (in % w/v).

11. The process as claimed in claim 1, wherein in the step (d) the concentration of dipotassium hydrogen phosphate for fermentation media is 0.01 (in % w/v).

12. The process as claimed in claim 1, wherein in the step (d) the concentration of ferrous sulphate for fermentation media is 0.005 (in % w/v).

13. The process as claimed in claim 1, wherein in the step (d) the concentration of magnesium sulphate for fermentation media is 0.05 (in % w/v).

14. The process as claimed in claim 1, wherein in the step (d) the concentration of cottonseed flour is 4% w/v, which serves as an organic nitrogen source and an inducer for xylitol production.

15. The process as claimed in claim 1, wherein the pH of the medium of step (d) is about 6.0.

16. The process as claimed in claim 1, wherein the stirring of step (d) is performed at the at of 200–300 RPM.

17. The process as claimed in claim 1, wherein in the step (d) a fermentation time of 60–72 hrs is required for maximum conversion of xylose to xylitol.

18. The process as claimed in claim 1, wherein the xylitol is obtained using conventional method from fermentation broth of step (d).

19. The process as claimed in claim 1, wherein high fermentation yields of 0.94 to 0.99 g xylitol/g xylose are obtained.

* * * * *